US008481500B2

(12) United States Patent
Almau et al.

(10) Patent No.: US 8,481,500 B2
(45) Date of Patent: Jul. 9, 2013

(54) COMPOUNDS HAVING NEUROPROTECTIVE PROPERTIES

(75) Inventors: Carlos Matute Almau, Leioa-Vizcaya (ES); Maria Victoria Sanchez Gomez, Leioa-Vizcaya (ES); Rosario Campos Esparza, Leoia-Vizcaya (ES); Elena Alberdi Alfonso, Leioa-Vizcaya (ES); Miroslav Gottlieb, Leioa-Vizcaya (ES); Gaskon Ibarretxe Bilbao, Leioa-Vizcaya (ES); Jose Maria Delgado Garcia, Sevilla (ES); Agnes Gruart I Masso, Sevilla (ES); Rocio Leal Campanario, Sevilla (ES)

(73) Assignees: Universidad del Pais Vasco, Leioa-Vizcaya (ES); Universidad Pablo de Olavide, Seville (ES)

( * ) Notice: Subject to any disclaimer, the term of this patent is extended or adjusted under 35 U.S.C. 154(b) by 617 days.

(21) Appl. No.: 12/159,781

(22) PCT Filed: Dec. 29, 2006

(86) PCT No.: PCT/ES2006/000727
§ 371 (c)(1),
(2), (4) Date: Oct. 8, 2008

(87) PCT Pub. No.: WO2007/077279
PCT Pub. Date: Jul. 12, 2007

(65) Prior Publication Data
US 2009/0131339 A1    May 21, 2009

(30) Foreign Application Priority Data
Dec. 30, 2005  (ES) .................................. 200503262

(51) Int. Cl.
*A61K 31/70*  (2006.01)
(52) U.S. Cl.
USPC .............................................. 514/23; 514/25
(58) Field of Classification Search
USPC ..................................................... 514/25, 23
See application file for complete search history.

(56) References Cited

U.S. PATENT DOCUMENTS

2003/0055103 A1  3/2003  Heinzen et al.
2005/0009760 A1*  1/2005  Wang et al. ...................... 514/27

FOREIGN PATENT DOCUMENTS

| JP | 2005-104850 A | 4/2005 |
| WO | 0149281 A2 | 7/2001 |
| WO | 2006001665 A1 | 1/2006 |

OTHER PUBLICATIONS

Yoshimi et al, Cancer Letters, vol. 163, 2001, pp. 163-170.*
Leiro et al, Biochemical Pharmacology, vol. 65, issue 8, Apr. 15, 2003, pp. 1361-1371.*
Carriedo, S. et al., "AMPA Exposures Induce Mitochondrial Ca21 Overload and ROS Generation in Spinal Motor Neurons In Vitro", "The Journal of Neuroscience", Jan. 1, 2000, pp. 240-250, vol. 20, No. 1.
Choi, D., "Ischemia-induced neuronal apoptosis", "Current Opinion in Neurobiology", 1996, pp. 667-672, vol. 6.
Gilgun-Sherki, Y. et al., "Antioxidant Therapy in Acute Central Nervous System Injury: Current State", "Pharmacological Reviews", 2002, vol. 54, No. 2, Publisher: The American Society for Pharmacology and Experimental Therapeutics.
Gottlieb, M. et al., "Neuroprotection by two polyphenols following excitotoxicity and experimental ischemia", "Neurobiology of Disease", Jun. 27, 2006, pp. 374-386, vol. 23.
Ikonomidou, C. et al. , "Why did NMDA receptor antagonists fail clinical trials for stroke and traumatic brain injury?", "Lancet Neurology", 2002, pp. 383-386, vol. 1.
Kim, Hee, et al. , "Effects of naturally occurring compounds on fibril formation and oxidative stress of beta-amyloid", "J. Agric. Food Chem.", Sep. 30, 2005, pp. 8537-8541, vol. 53, No. 22.
Mandel, S. et al., "Cell signaling pathways in the neuroprotective actions of the green tea polyphenol (−)-epigallocatechin-3-gallate;", "Journal of Neurochemistry", 2004, pp. 1-15, vol. 88, No. 1555.
Matute, Carlos, et al., "The link between excitotoxic oligodendroglial death and demyelinating diseases", "Trends in Neurosciences", Apr. 2001, pp. 224-230, vol. 24, No. 4.
Matute, C. et al., "Excitotoxicity in glial cells", "European Journal of Pharmacology", 2002, pp. 239-246, vol. 447.
Sanchez-Gomez, M. et al., "Caspase-Dependent and Caspase-Independent Oligodendrocyte Death Mediated by AMPA and Kainate Receptors", "The Journal of Neuroscience", Oct. 22, 2003, pp. 9519-9528, vol. 23, No. 29.
Kim, Hee, et al., "Effects of naturally occurring compounds on fibril formation and oxidative stress of beta-amyloid (Abstract Only)", "J. Agric. Food Chem.", Sep. 30, 2005, pp. 8537-8541, vol. 53, No. 22.
Behl, C., "Alzheimer's Disease and Oxidative Stress: Implications for Novel Therapeutic Approaches", "Progress in Neurobiology", 1999, pp. 301-323, vol. 57.
Hayashi, T., et al., "Molecular Mechanisms of Ischemic Neuronal Cell Death—With Relevance to Alzheimer's Disease", "Current Alzheimer Research", 2006, pp. 351-358, vol. 3.
Lees, K.R., et al., "NXY-059 for Acute Ischemic Stroke", "The New England Journal of Medicine", 2006, pp. 588-600, vol. 354, No. 6.

(Continued)

*Primary Examiner* — Elli Peselev
(74) *Attorney, Agent, or Firm* — Hultquist, PLLC; Steven J. Hultquist; Kelly K. Reynolds

(57) ABSTRACT

The invention relates to the use of morin and mangiferin, the pharmaceutically acceptable salts, prodrugs and/or solvates thereof in the production of a pharmaceutical composition for the prevention and/or treatment of a neurodegenerative disease and symptoms associated with ageing, as well as to food compositions comprising said compounds.

12 Claims, 4 Drawing Sheets

OTHER PUBLICATIONS

Muir, K.W., et al., "Clinical Experience with Excitatory Amino Acid Antagonist Drugs", "American Heart Association", 1995, pp. 503-513, vol. 26.

Tarawneh, R., et al., "Potential Future Neuroprotective Therapies for Neurodegenerative Disorders and Stroke", "Clin Geriatr Med.", 2010, pp. 125-147, vol. 26, No. 1.

* cited by examiner

Figures 2 A-D, a-d

COMPOUNDS HAVING NEUROPROTECTIVE PROPERTIES

CROSS-REFERENCE TO RELATED APPLICATIONS

This application is the U.S. national phase filed under the provisions of 35 USC §371 of International Application No. PCT/ES06/00727 filed Dec. 29, 2006, which in turn claims priority of Spanish Patent Application No. P200503262 filed Dec. 30, 2005. The disclosures of such international application and Spanish priority application are hereby incorporated herein by reference in their respective entireties, for all purposes.

FIELD OF THE ART

The invention relates to the use of antioxidant compounds in the prevention and/or treatment of neurodegenerative diseases and symptoms associated with ageing, and with a food composition comprising said antioxidants.

STATE OF THE ART

Neurodegenerative diseases are a social healthcare problem of great importance which is aggravated in Western societies by the progressive ageing of the population. These diseases present loss of central nervous system cells caused by different genetic or environmental causes which are still not completely known and which cause physical and cognitive deterioration aggravated over time.

The main pathophysiological processes generated in strokes involve the lack of energy, loss of cell homeostasis, acidosis, increase of intracellular calcium, excitotoxicity and toxicity mediated by free radicals. Transient cerebral ischemia, an animal cardiac arrest and stroke model, induces molecular alterations causing neuronal hyperexcitability and cell death in vulnerable regions of the brain such as the CA1 hippocampus area (Choi, *Curr. Opin. Neurobiol.* 6, 667, 1996). Ischemia results in the loss of ATP which reduces the function of glutamate carriers which normally eliminate the glutamate released from the synaptic cleft. The resulting increase of glutamate in the extracellular space causes the excessive activation of glutamate receptors and the pathological increase in the intracellular calcium levels culminating with neuron and glial cell death (Choi, *Curr. Opin. Neurobiol.* 6, 667, 1996; Matute et al., *Eur. J. Pharmacol.* 447, 239, 2002). However, glutamate antagonist receptors have not been efficient in clinical stroke conditions (Ikonomidou and Turski, *Lancet Neurol.* 1, 383, 2002).

Like neurons, oligodendrocytes are sensitive to excitotoxic stimuli mediated by the overactivation of their ionotropic AMPA/kainate glutamate receptors (Matute et al. *Trends Neurosc.* 24, 224, 2001). The overactivation of glutamate receptors in neurons and oligodendrocytes causes sudden increases in the concentration of cytoplasmic $Ca^{2+}$ ions in both types of cells. An important intracellular target for the toxicity mediated by $Ca^{2+}$ ions is the mitochondrion, which can accept high charges of this cation in an electric potential-dependent manner, which occurs as a result of excitotoxic stimuli (Carriedo et al., *J. Neurosci* 20, 240, 2000; Sánchez-Gómez et al., *J. Neurosci.* 23, 9519, 2003).

Given that both excitotoxicity stimuli and ischemia/reperfusion generate oxidative stress, it is conceivable that the administration of antioxidants can limit oxidative damage and reduce the progression of the disease. In fact, a number of exogenously administered antioxidants have proved to be neuroprotective in experimental cerebral ischemia models; however, most of them did not show beneficial effects in clinical trials (Gilgun-Sherki et al., *Pharmacol. Rev.* 4, 71, 2002). The problem for converting experimental results with antioxidants into effective treatments for strokes is at least partly due to the unsuitable access of the selected drugs in the recoverable regions of the ischemia area, and to an insufficient characterization of the alteration of cognitive functions in diseased animal models.

The therapeutic potential of new antioxidants, especially those of natural origin, has additionally been assayed. In this sense, flavonoids and other polyphenol antioxidants present as bioactive molecules in vegetables, fruits and red wine have proved to be potentially beneficial in neurodegenerative diseases associated with oxidative stress (Mandel et al., *J. Neurochem.*, 88, 1555, 2004).

Likewise, document JP2005104850 describes the use of some specific polyphenols for the prevention of Alzheimer's disease by means of a mechanism for controlling and suppressing β-amyloid fiber deposition in brain tissue. However, their action against neurodegenerative diseases caused by cell or oligodendrial death is not specified.

There is therefore a need in the state of the art to find other compounds having suitable neuroprotective and therapeutic properties for the treatment of diseases mediated by cell death and which can suitably access the regions of the brain affected by said mechanism.

SUMMARY OF THE INVENTION

The inventors have surprisingly found that the compounds of formula (I), specifically morin or mangiferin, reduce oxidative stress and that this property effectively reduces neuronal and oligodendrial death in cell and animal neurodegenerative disease models. The results can be extrapolated for therapeutic or prophylactic purposes in the risk population. Given that they are compounds with a very low toxicity profile, their use as a drug or in a food composition is very suitable and does not require complex clinical trials as occurs with conventional drugs.

This new application of the compounds of formula (I) is based on the research conducted by the inventors on cell models in neuron and oligodendrocyte cultures, where the effective reduction of the oxidative stress caused by lethal stimuli, protecting these cells from death, has been shown. Likewise, in experimental animals subjected to transient cerebral ischemia, it has been observed that the administration of antioxidants such as morin and mangiferin half an hour after the ischemia reduces post-ischemic brain damage and attenuates the cognitive deterioration caused by said pathological circumstance. Therefore, these antioxidants have a high efficiency in reducing tissue damage and the neurological symptoms caused by central nervous system lesions. The neuroprotective capacity of the compounds of formula (I), and very especially of morin and mangiferin, is furthermore higher than that of other antioxidants assayed in the state of the art. Likewise, given that many of the symptoms related to ageing are mediated by cell and oligodendrial death, these compounds can be very useful for treating the mentioned symptoms.

Therefore, in an aspect, the invention relates to the use of a compound of formula (I) in the production of a pharmaceutical composition for the prevention and/or treatment of a neurodegenerative disease.

In an additional aspect, the invention is aimed at the use of a compound of formula (I) in the production of a pharmaceutical composition for the prevention and/or treatment of the symptoms associated with ageing.

In another aspect, the invention relates to a method for the prevention and/or treatment of a neurodegenerative disease in an individual suffering from said neurodegenerative disease, which comprises administering a therapeutically effective amount of a compound of formula (I) to said individual.

In another aspect, the invention relates to a method for the prevention and/or treatment of the symptoms associated with ageing in an individual suffering from said symptoms, which comprises administering a therapeutically effective amount of a compound of formula (I) to said individual.

The use of a compound of formula (I) in the prevention and/or treatment of neurodegenerative diseases involves an effective way of preventing the problems put forth by current strategies, such as the impossibility of obtaining effective results in clinical trials as well as the toxicity of some of the compounds used in the treatment of said neurodegenerative diseases.

In an additional aspect, the invention relates to a food composition comprising a compound of formula (I) and a food carrier.

BRIEF DESCRIPTION OF THE DRAWINGS

FIG. 2 shows the superoxide production in the CA1 region of the hippocampus after the ischemia. FIGS. 2 A-D specifically correspond to a panoramic view showing the fluorescence emitted by oxidized hydroethidine in the pyramidal layer of the CA1 region after the ischemia; A: for control rats; B: for rats treated with placebo; C: for rats treated with mangiferin; D: for rats treated with morin.

FIGS. 2 a-d in turn correspond to a detailed view of the fluorescence levels detected inside the cytoplasm of the cells in the pyramidal layer of the CA1 region; A: for control rats; B: for rats treated with placebo; C: for rats treated with mangiferin; D: for rats treated with morin.

DETAILED DESCRIPTION OF THE INVENTION

Figure 1A:
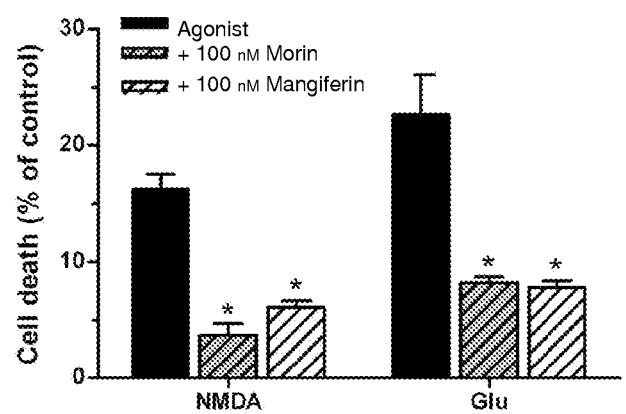
FIG. 1A shows the percentage of neuron death caused by excitotoxic stimuli (glutamate or NMDA) in cell cultures and the effect caused by the addition of morin and mangiferin.

In one aspect, the invention relates to the use of a compound of formula (I):

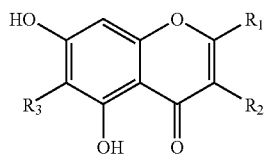

(I)

wherein $R_1$ is either

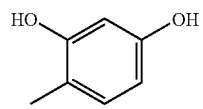

or forms together with $R_2$ the

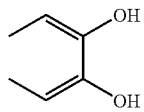

group $R_2$ is either OH or forms together with $R_1$ the

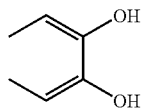

group $R_3$ is either OH or the

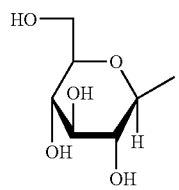

group
such that:
when $R_1$ and $R_2$ together form a

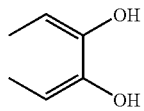

group, $R_3$ is

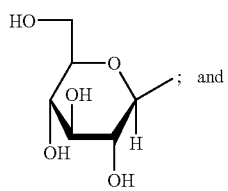

when $R_2$ and $R_3$ are OH, $R_1$ is

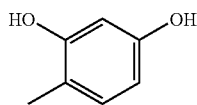

the pharmaceutically acceptable salts, prodrugs and/or solvates thereof, in the production of a pharmaceutical composition for the prevention and/or treatment of a neurodegenerative disease.

In another aspect, the invention relates to the use of a compound of formula (I):

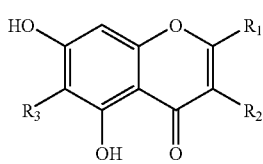 (I)

wherein $R_1$ is either

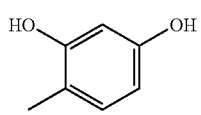

or forms together with $R_2$ the

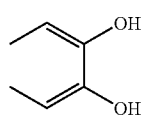

group $R_2$ is either OH or forms together with $R_1$ the

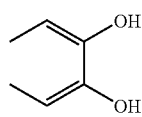

group $R_3$ is either OH or the

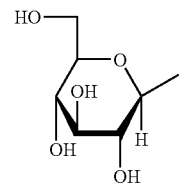

group
such that:
when $R_1$ and $R_2$ together form a

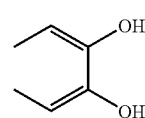

group, $R_3$ is

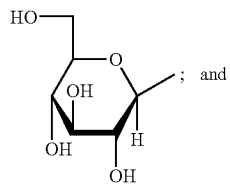

when $R_2$ and $R_3$ are OH, $R_1$ is

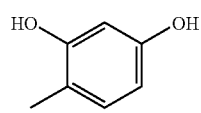

the pharmaceutically acceptable salts, prodrugs and/or solvates thereof, in the production of a pharmaceutical composition for the prevention and/or treatment of symptoms associated with ageing.

The compound of formula (I) with the cresol moiety as $R_1$ is called morin (compound of formula Ia) and the compound of formula (I) with the glucoside moiety as $R_3$ is called mangiferin (compound of formula Ib).

As used herein, the term "pharmaceutically acceptable salts" relates to any salt of the compound of formula (I) which can be used in the production of a medicinal product. The nature of the salt is not critical provided that it is pharmaceutically acceptable. The pharmaceutically acceptable salts of the compound of formula (I) include, for example, alkaline salts, which can be formed from the reaction of a compound of formula (I) with a stoichiometric amount of the suitable base in water, in an organic solvent or in a mixture of both. Alkaline salts include inorganic salts such as for example sodium, potassium, calcium, ammonium, magnesium, aluminium and lithium salts.

Likewise, the prodrugs of a compound of formula (I) are within the scope of this invention. As used herein, the term "prodrug" includes any derivative compound of the compound of formula (I), for example an ester, etc., which, when it is administered to an individual, can directly or indirectly provide a compound of formula (I) in said individual. Said derivative is advantageously a compound increasing the bioavailability of the compound of formula (I) when it is administered to an individual or enhancing the release of said compound of formula (I) in a biological compartment. The nature of said derivative is not critical provided that it can be administered to an individual and provides a compound of formula (I) in a biological compartment of an individual. Said prodrug can be prepared by means of conventional methods known by persons skilled in the art.

The compound of formula (I) can be obtained in free base or salt form. In both cases it is preferably obtained in crystalline form, both as free compounds and solvates (for example, hydrates), both forms being included within the scope of the present invention. The salvation methods are generally known in the state of the art. In a particular case of the present invention, the compound of formula (I) called morin is coordinated with two water molecules.

Among the compounds of formula (I), morin (Ia) is present in the wood of the species called *Chlorophora tinctoria*, Moraceae. Alternatively, said compound can be obtained by known methods, for example, from the condensation reaction of fluoroacetophenone dimethyl ether with 2,4-dimethoxybenzaldehyde by means of the process described by von Kostanecki et al., *Ver.* 39, 625, 4014 (1906).

Mangiferin (Ib) is in turn the C-glucoside of tetrahydroxy-1,3,6,7-xanthone. Although it can be extracted from a number of plant species, it is more widely distributed in the plant also called mangiferin and especially in the angiosperms.

In a particular embodiment, for its administration in the prevention and/or treatment of neurodegenerative diseases as well as of symptoms associated with ageing, the compound of formula (I), the pharmaceutically acceptable salts, prodrugs and/or solvates thereof, are formulated in a suitable pharmaceutical composition in the therapeutically effective amount, together with one or more pharmaceutically acceptable carriers, adjuvants or excipients.

The pharmaceutical compositions can be administered by any suitable method of administration, for example, orally, parenterally (for example, subcutaneously, intraperitoneally, intravenously, intramuscularly, etc.), rectally, etc., typically orally due to the chronic nature of the disease to be treated.

In a particular embodiment, said pharmaceutical compositions can be in a dosage form for oral administration, either in solid or liquid form. Illustrative examples of dosage forms for oral administration include tablets, capsules, granulates, solutions, suspensions, etc., and can contain conventional excipients, such as binders, diluents, disintegrants, lubricants, wetting agents, etc., and can be prepared by conventional methods. The pharmaceutical compositions can also be adapted for their parenteral administration, in the form of, for example, sterile solutions, suspensions or lyophilized products, in the suitable dosage form; in this case, said pharmaceutical compositions will include the suitable excipients, such as buffers, surfactants, etc. In any case, the excipients will be chosen according to the selected dosage form of administration. A review of the different dosage forms for drug administration and their preparation can be found in the book "*Tratado de Farmacia Galénica*", by C. Faulí i Trillo, 10th Edition, 1993, Luzán 5, S.A. de Ediciones.

For its application in therapy, the compound of formula (I) will preferably be in a pharmaceutically acceptable or substantially pure form, i.e., the compound of formula (I) has a pharmaceutically acceptable purity level excluding the pharmaceutically acceptable excipients and not including material considered to be toxic at normal dosage levels. The purity levels for a compound of formula (I) are preferably greater than 50%, more preferably greater than 70%, more preferably greater than 90%. In a preferred embodiment, they are greater than 95%.

The therapeutically effective amount of the compound of formula (I) to be administered will generally depend, among other factors, on the individual to be treated, on the severity of the disease that said individual suffers from, on the chosen form of administration, etc. For this reason, the doses mentioned in this invention must only be considered as guidelines for the person skilled in the art, and the dose must be adjusted according to the aforementioned variables. Nevertheless, a compound of formula (I) can be administered one or more times a day, for example, 1, 2, 3 or 4 times a day, in a typical total daily amount comprised between 5 and 20 mg/kg of body mass/day, preferably 10 mg/kg body mass/day.

The compound of formula (I), the pharmaceutically acceptable salts, prodrugs and/or solvates thereof, as well as the pharmaceutical compositions containing them can be used together with other additional drugs useful in the prevention and/or treatment of neurodegenerative diseases, for example, with thrombin inhibitors, to provide a combination therapy. Said additional drugs can form part of the same pharmaceutical composition or, alternatively, they can be provided in the form of a separate composition for its simultaneous or non-simultaneous administration with regard to the administration of the pharmaceutical composition comprising a compound of formula (I), or a prodrug, solvate or a pharmaceutically acceptable salt thereof.

Likewise, the compound of formula (I), the pharmaceutically acceptable salts, prodrugs, and/or solvates thereof, as well as the pharmaceutical compositions containing them can be used together with other additional drugs useful in the prevention and/or treatment of symptoms associated with ageing, to provide a combination therapy. Said additional drugs can form part of the same pharmaceutical composition or, alternatively, they can be provided in the form of a separate composition for its simultaneous or non-simultaneous administration with regard to the administration of the pharmaceutical composition comprising a compound of formula (I), or a prodrug, solvate or a pharmaceutically acceptable salt thereof.

In a particular embodiment, the invention is aimed at the use of a compound of formula (I), the pharmaceutically acceptable salts, prodrugs and/or solvates thereof, in the production of a pharmaceutical composition for the prevention and/or the treatment of a neurodegenerative disease. Assays conducted by the inventors have shown that the administration of mangiferin and morin, compounds of formula (I), to mice in which transient cerebral ischemia has been induced, causes a significant increase of positive NeuN[+] cells in the pyramidal layer of the CA1 hippocampus after 7 and 70 days post-ischemia (Example 3). For the purposes of the present invention, neurodegenerative disease is understood as any disease caused as result of neuronal and/or oligodendrial death in vulnerable regions of the brain and mediated by excitotoxic stimuli, such as cerebral ischemia, Creutzfeldt-Jakob disease, Huntington's disease, Lewy body disease, Parkinson's disease, Pick's disease, amyotrophic lateral sclerosis, neurofibromatosis, brain damage, cerebrovascular accident, multiple sclerosis, memory loss or multi-infarct dementia. Likewise, the diseases caused by β-amyloid fiber deposition in brain tissue, as is the case of Alzheimer's disease, would be comprised in the definition of neurodegenerative disease.

In a particular embodiment, a compound of formula (Ia) called morin:

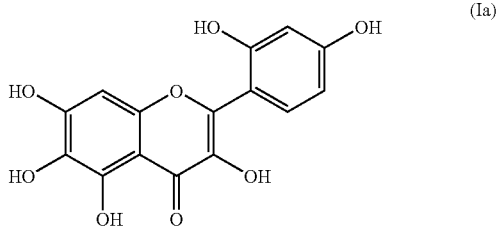 [SMILES: O=c1c(O)c(-c2ccc(O)cc2O)oc2cc(O)c(O)c(O)c12]

the pharmaceutically acceptable salts, prodrugs and/or solvates thereof, are used in the production of a composition for the prevention and/or treatment of a neurodegenerative disease caused as a result of neuronal and/or oligodendrial death, selected from cerebral ischemia, Creutzfeldt-Jakob disease, Huntington's disease, Lewy body disease, Parkinson's disease, Pick's disease, amyotrophic lateral sclerosis, neurofibromatosis, brain damage, cerebrovascular accident, multiple sclerosis, memory loss and multi-infarct dementia.

In another particular embodiment, a compound of formula (Ib) called mangiferin:

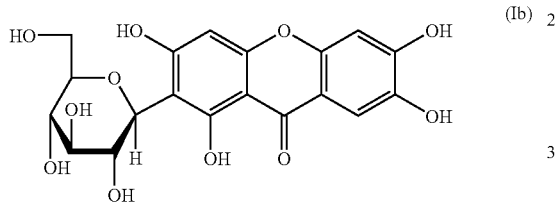

the pharmaceutically acceptable salts, prodrugs and/or solvates thereof, are used in the production of a composition for the prevention and/or treatment of a neurodegenerative disease caused as a result of neuronal and/or oligodendrial death as well as for the prevention and/or treatment of a neurodegenerative disease caused by β-amyloid fiber deposition, selected from cerebral ischemia, Creutzfeldt-Jakob disease, Huntington's disease, Lewy body disease, Parkinson's disease, Pick's disease, amyotrophic lateral sclerosis, neurofibromatosis, brain damage, cerebrovascular accident, multiple sclerosis, memory loss, multi-infarct dementia and Alzheimer's disease.

In another aspect, the invention relates to a method for the prevention and/or treatment of a neurodegenerative disease, in an individual suffering from said neurodegenerative disease, which comprises administering a therapeutically effective amount of a compound of formula (I), or one of the pharmaceutically acceptable salts, prodrugs and/or solvates thereof, to said individual. The characteristics of the administration, pharmaceutical composition and therapeutically effective amount of the compound of formula (I) have been previously defined.

In a particular embodiment, said neurodegenerative disease, which is prevented and/or treated according to the method of the present invention, is caused as a result of neuronal and oligodendrial death as well by β-amyloid fiber deposition in brain tissue. In a specific embodiment, said neurodegenerative disease is cerebral ischemia, Creutzfeldt-Jakob disease, Huntington's disease, Lewy body disease, Parkinson's disease, Pick's disease, amyotrophic lateral sclerosis, neurofibromatosis, brain damage, cerebrovascular accident, multiple sclerosis, memory loss, multi-infarct dementia or Alzheimer's disease, preferably cerebral ischemia.

In another particular embodiment, said neurodegenerative disease, which is prevented and/or treated according to the method of the present invention, is caused as a result of neuronal and oligodendrial death. In a specific embodiment, said neurodegenerative disease is cerebral ischemia, Creutzfeldt-Jakob disease, Huntington's disease, Lewy body disease, Parkinson's disease, Pick's disease, amyotrophic lateral sclerosis, neurofibromatosis, brain damage, cerebrovascular accident, multiple sclerosis, memory loss or multi-infarct dementia, preferably cerebral ischemia.

In another particular embodiment, the invention is aimed at the use of a compound of formula (I), the pharmaceutically acceptable salts, prodrugs and/or solvates thereof, in the production of a pharmaceutical composition for the prevention and/or the treatment of the symptoms associated with ageing. Some examples of these symptoms would be memory loss, learning difficulty, reduction of cognitive functions, among others.

In another aspect, the invention relates to a method for the prevention and/or treatment of the symptoms associated with ageing, in an individual suffering from said symptoms, which comprises administering a therapeutically effective amount of a compound of formula (I), or one of the pharmaceutically acceptable salts, prodrugs and/or solvates thereof, to said individual. The characteristics of the administration, pharmaceutical composition and therapeutically effective amount of the compound of formula (I) have been previously defined.

As used in this description, the term "individual" relates to any mammal and includes, although it is not limited to, domestic animals, rodents, primates and humans. Said individual is preferably a male or female human being of any age or race.

In another aspect, the invention relates to a food composition comprising a compound of formula (I) such as that described in the present invention and a food carrier. For the purposes of the present invention, a food carrier is understood as any product which can be used in human or animal food. The choice of the suitable food carrier can be made by a person skilled in the art from conventional food carriers existing in the state of the art.

Said food composition can be in the form of soluble powder, a liquid concentrate, a snack or it can be a ready to be used formulation suitable for oral consumption or enteral administration. Examples of these compositions can be, among others, a dairy product or derivative thereof such as a shake, milk, including flavored or fermented milk, a yogurt, etc.; a juice; a floury product or derivative thereof such as a cake, a bread, a cookie; an oil, a candy such as a chewing gum, a sweet, etc.

In an additional aspect, the invention relates to the use of a compound of formula (I) for the preparation of a food composition for the prevention and/or improvement of a neurodegenerative disease. Likewise, the invention is also aimed at the use of a compound of formula (I) for the preparation of a food composition for the prevention and/or improvement of symptoms associated with ageing.

The amount of the compound of formula (I) included in the food composition which can be ingested by a patient will depend on a number of factors such as the condition of the patient, his or her body weight, age, among others. However, the suitable amount must be prescribed by a specialist and it will be adjusted depending on the aforementioned variables. Nevertheless, a compound of formula (I) can be administered in several doses, for example from 2 to 5 times a day, for the purpose of administering the recommended daily amount or it can be taken in a single dose.

The following examples illustrate the invention and must not be considered as limiting the scope thereof.

EXAMPLES

Example 1

Assessment of the Effect of the Mangiferin and Morin Compounds in Neuron and Oligodendrocyte Cell Culture Death Cause by Submaximal Activation of Glutamate Receptors The neuron cultures were obtained from the brain cortex of Sprague Dawley rat embryos of 18 days of gestation (Larm et al., 1996, *Eur J Pharmacol* 314: 249-54; Cheung et al., 1998, *Neuropharmacol* 37: 1419-29). The cells were nourished Neurobasal medium supplemented with B27 supplement (Invitrogen). These cultures did not contain astrocytes or microglia and were used after 8 and 10 days in vitro.

The glutamate or NMDA (N-methyl-D-aspartate) agonists were applied, both at a concentration of 50 µM, for 10 minutes. The antioxidants, morin and mangiferin, were added during the exposure of the agonist at a concentration of 100 nM and were maintained in the medium for 3 hours until cell viability was measured by means of fluorescein diacetate. FIG. 1A shows how the addition of mangiferin or morin significantly attenuates excitotoxic neuronal death ($*p<0.001$, compared with the neurons treated only with agonist). The values are shown as the mean±S.E.M. of the quadruplicates from 3-4 different experiments.

Figure 1B:
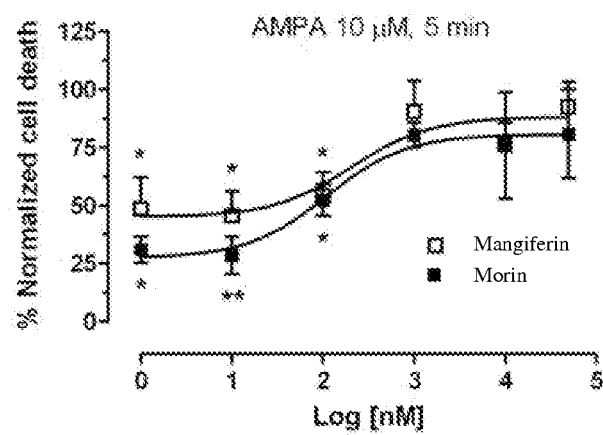
FIG. 1B in turn shows the percentage of normalized cell death±S.E.M. caused by excitotoxic stimuli (glutamate or NMDA) in cell cultures and the effect caused by the addition of morin and mangiferin at different concentrations.
Figure 2E:
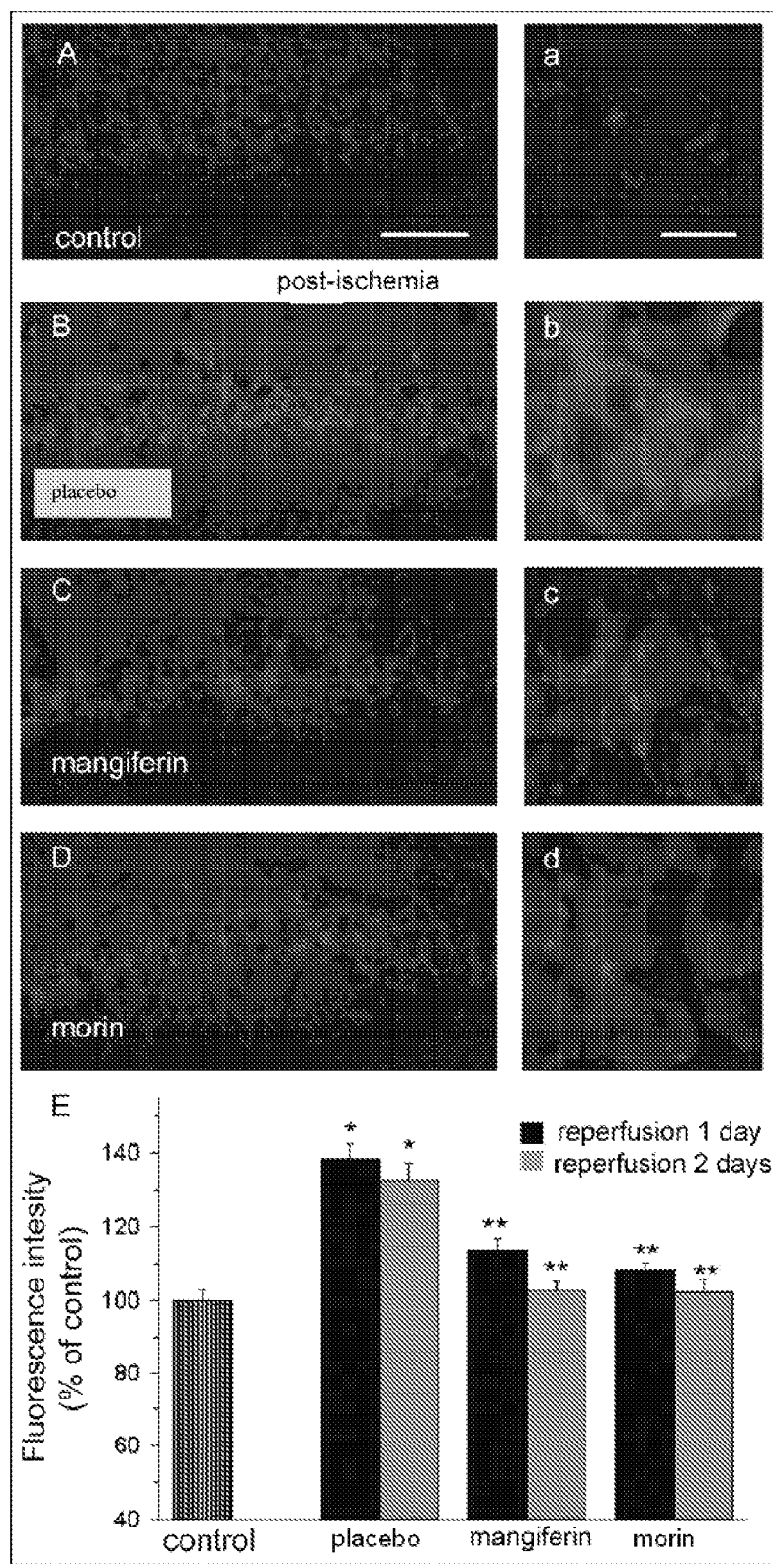
FIG. 2E shows the quantification of the fluorescence intensity (% with respect to controls rats) after 1 and 2 days post-ischemia (*$p<0.001$ compared to control rats, n=4; **$p<0.001$ compared to rats treated with placebo, n=3).

The oligodendrocyte cultures were in turn incubated with AMPA [(RS)-α-amino-3-hydroxy-5-methyl-4-isoxazolepropionic hydrobromic acid] agonists, at a 10 µM concentration for 5 minutes. The polyphenols, mangiferin and morin, were added 24 hours before the exposure of the agonist and until the end of the experiments at concentrations comprised between 10 and 100000 nM, and cell viability was measured by means of calcein fluorimetry 24 hours later. The values shown in FIG. 1B show the percentage of normalized cell death±S.E.M. of the triplicates according to the logarithm of the concentration from three different experiments. *: $p<0.05$; **: $p<0.01$.

As a whole, these results indicate that mangiferin and morin protect from neuronal and oligodendroglial death induced by excitotoxic stimuli which are relevant to those occurring in neurodegenerative diseases.

Example 2

Effect of Mangiferin and Morin in the Reduction of Superoxide Production in the CA1 Hippocampus Region after Ischemia Animals Four experimental groups of Sprague-Dawley rats (each group contained 20 animals) were randomly selected: control (C), ischemic (ISCH), ischemic animals treated with mangiferin (I+MNG), and ischemic animals treated with morin (I+MOR). Transient cerebral ischemia was induced by means of occlusion of the vertebral and common carotid arteries for 10 minutes. The criteria for determining cerebral ischemia were the bilateral loss of stretch reflex, limb stiffness and mydriasis. The rectal and body temperature was maintained at 37° C. during surgery and the ischemia. The animals which did not experience total loss of their reflexes or which did not experience an attack after the occlusion of the carotid artery were excluded from the study. The group of control animals was treated similarly to the group with ischemia, but none of their common carotid arteries was occluded.

Treatment

Mangiferin and morin were administered intraperitoneally at a concentration of 10 mg/kg of body weight, 30 minutes after the ischemic stimulus and then at a concentration of 5 mg/kg every 12 hours for 7 days.

Measurement of the Oxidative Stress In Vivo

The method described by Chan et al., 1998 (*J Neurosci* 18: 8292-99) was followed. After 24 and 48 post-ischemia, the animals were anesthetized with chloral hydrate (350 mg/kg) and hydroethidine (8 mg/kg) was administered to them through the jugular vein, being sacrificed 2 hours later. The fluorescence was examined in cryostat sections (10 µm) and was analyzed with a fluorescence microscope (Zeiss Axiophot). The images were taken with a digital camera (Axio Vision, Zeiss) and analyzed with the Image Pro Plus program.

FIGS. 2A, 2B, 2C and 2D show a panoramic view of the fluorescence levels emitted by the oxidized hydroethidine in the neurons of the pyramidal layer of the CA1 region 1 day after the transient global ischemia, and the reduction by mangiferin and morin. FIGS. 2*a*, 2*b*, 2*c* and 2*d* show in detail the levels observed in the cytoplasm of these neurons. FIG. 2E quantifies the fluorescence (*$p<0.001$ compared with the control, n=4; **$p<0.001$ compared with rats treated with placebo, n=3), which corresponds to the 50 and 10 µm bar in the left and right columns, respectively.

Example 3

Assessment of the Effect of the Mangiferin and Morin Compounds in the Treatment of Transient Cerebral Ischemia in Rats The rats, treated as has been mentioned in Example 2, were profoundly anesthetized with chloral hydrate and transcardially perfused with a fixer after 7 and 70 days post-ischemia (n=4-5 in each group). The fixing solution consisted of 4% paraformaldehyde in 0.1 M of sodium phosphate buffer, pH 7.4. The brains, once removed, were subsequently post-fixed for two hours at 4° C. in the same solution. Tissue was obtained from the operated and non-operated control rats (n=4-5 in each group). Cryostatic sections (10 µm) were collected at the dorsal hippocampus level in gelled plates (slides) and were processed for the immunohistochemical assays as has been previously described (Gottlieb and Matute, 1997, *J Cereb Blood Flow Metab.:* 290-300). NeuN mice monoclonal antibodies (2 µg/ml; Chemicon, Temecula Calif.) for microtubule-associated protein 2 (MAP2; 4 µg/ml; Sigma) and CD11b (OX42; 10 µg/ml; Serotec Ltd., Oxford, England) were used. As a negative control, in all the experiments different sections were incubated with non-immune normal mice immunoglobulins (0.5 mg/ml). A preliminary evaluation was conducted of the post-ischemic damage in each brain using toluidine blue as the histogical stain.

The number of positive NeuN cells was quantified in the pyramidal layer of the CA1 hippocampus in control rats and operated rats, and in animals subjected to transient cerebral ischemia 7 and 70 days after the reperfusion (n=4-5 animals for every experimental group). The amounts were collected both from the left and the right hemisphere of each section analyzed by immunohistochemistry, with two sections for every experiment from at least three independent experiments. The immunostaining levels with anti-MAP2 antibodies were measured from photographs taken with a digital camera (AxioVision, Zeiss) with a 4× magnification, which were subsequently processed by an image analysis program (Image Pro Plus v4.5) to obtain an 8-bit image of grays of the entire CA1 region for the purpose of determining the value of the specific density of grays.

Figure 3:
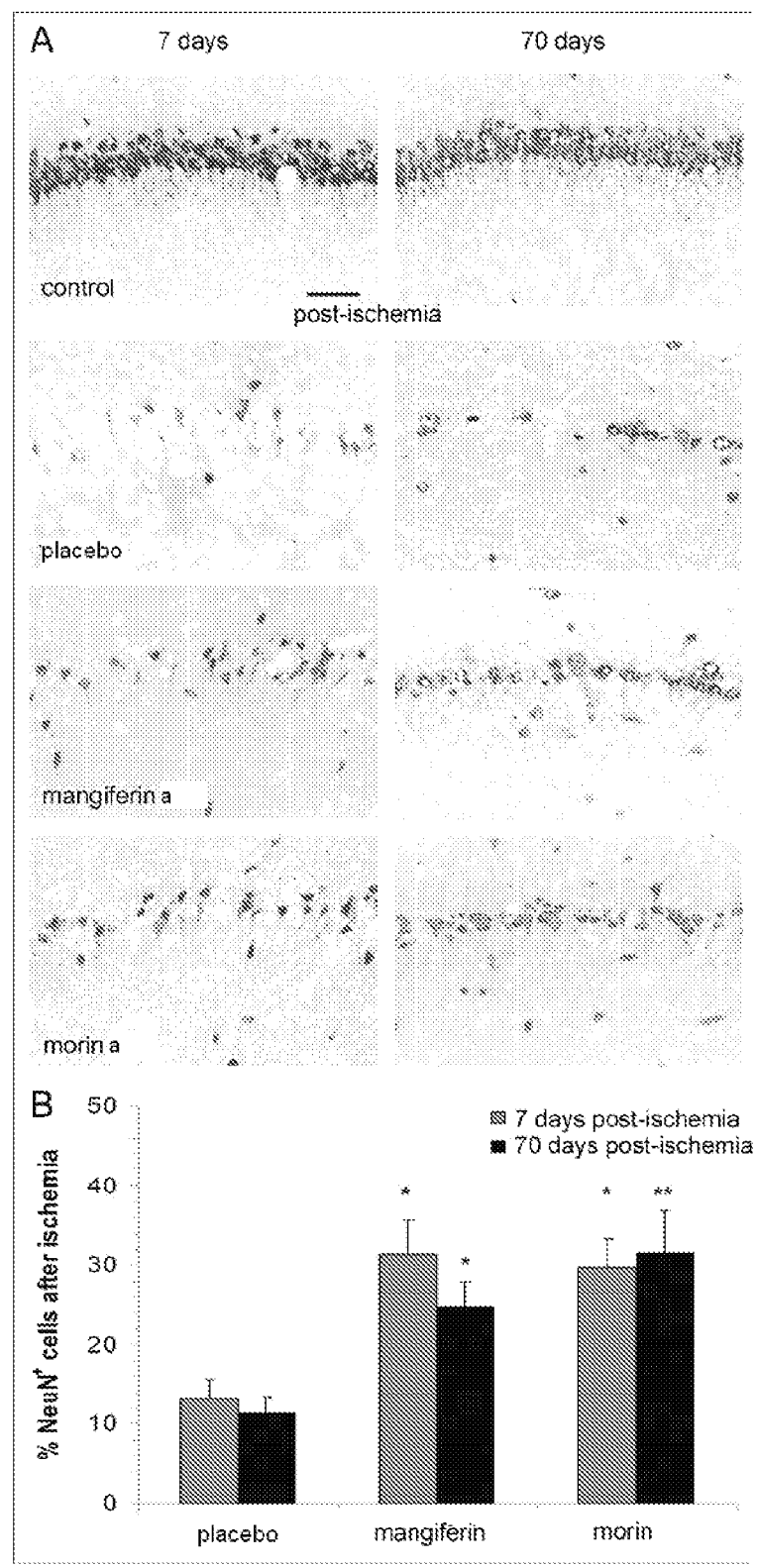
FIG. 3A shows the amount of NeuN$^+$ cells in control animals and in animals subjected to ischemia 7 and 70 days after the operation treated with placebo, with mangiferin and with morin.
FIG. 3B shows the percentage of NeuN$^+$ cells 7 and 70 days after the ischemia in animals treated with placebo, with mangiferin and with morin.

FIG. 3 shows how the number of NeuN neurons labeled with antibodies in post-ischemic CA1 regions increases after the treatment with polyphenols. The left and right columns of FIG. 3A represent the NeuN+ cells 7 and 70 days after the operation. Rows one to four show the appearance of staining in operated animals (control) and in animals treated with placebo, mangiferin or morin after the ischemia. It must be indicated that the area and the number of neurons in the pyramidal layer observed in the operated rats (upper row) is drastically reduced in animals subjected to ischemia and subsequent treatment with placebo at the post-ischemia times studied. In contrast, the ischemic stimulus followed by the treatment with mangiferin or with morin causes a larger number of neurons in the pyramidal layer. The calibration bar is 100 μm. FIG. 3B shows the number of NeuN+ cells in animals treated with placebo compared with operated rats (100%). The number of NeuN+ cells is larger in animals treated with mangiferin or with morin compared with the animals treated with placebo (*p<0.05, ++p<0.01) 7 and 70 days after the ischemia. The number of NeuN+ cells refers to 100%. Each bar represents the mean±S.E.M. of counts obtained from two sections of the right and left hippocampus from 4-5 animals.

Example 4

Assessment of the Effect of the Mangiferin and Morin Compounds in a Quantitative Analysis of Conditioned Eyelid Responses The study of the eyelid responses by means of classic conditioning was carried out in 10 Sprague-Dawley rats per experimental group. Each animal was anesthetized with ketamine (100 mg/kg) and xylazine (20 mg/kg). The stimulating electrodes were placed in the left supraorbital branch of the trigeminal nerve, and the recording electrodes in the ipsilateral orbicular muscle, as has been described in detail in Gruart et al., 1995, *J Neurophysiol* 74: 226-49. The classic conditioning was achieved by means of the paradigm shown in the upper part of FIG. 4.

Figure 4:
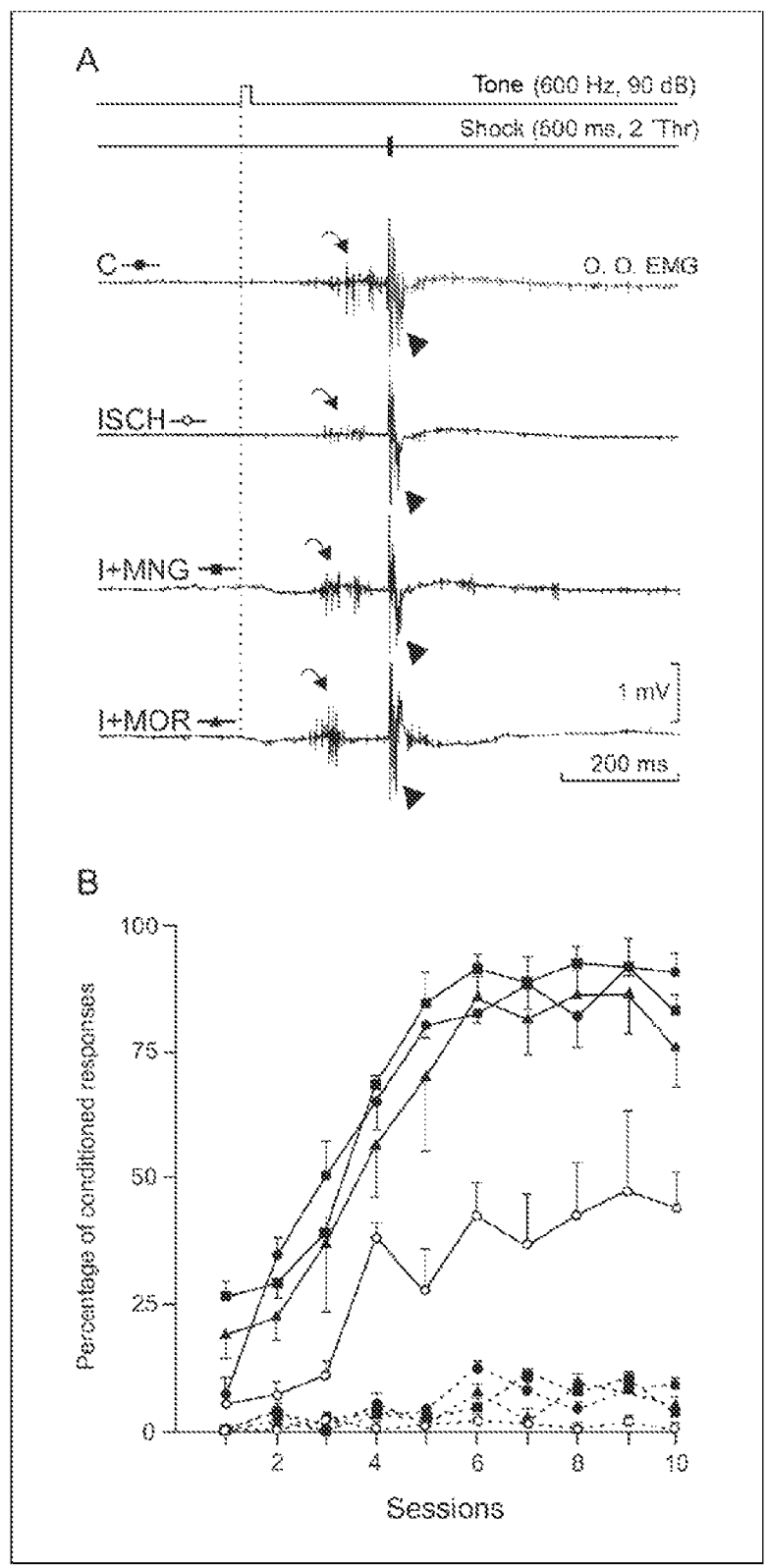
FIG. 4A shows the electromyographic response obtained for: (C) control rats; (ISCH): rats with ischemia; (I+MNG): rats with ischemia treated with mangiferin; (I+MOR): rats with ischemia treated with morin.
FIG. 4B shows the average percentage of conditioned responses over 10 conditioned sessions for the conditioned (solid lines) and pseudo-conditioned (dotted lines) groups: (black circles): control rats; (white circles): rats with ischemia; (squares): rats with ischemia treated with mangiferin; (triangles): rats with ischemia treated with morin.

A quantitative analysis of the classically conditioned eyelid responses from control mice (C, dotted line) and mice with ischemia (ISCH, circles), and from mice with ischemia treated with mangiferin (I+MNG, squares) or morin (I+MOR, triangles), is shown in FIG. 4. Specifically, FIG. 4A corresponds the electromyographic responses (EMG, in mV) obtained from representative animals of each of indicated the experimental groups collected during the ninth session. For the conditioning signal, a tone (600 Hz, 90 dB) is applied for 20 ms as the conditioning stimulus (CS). The tone was followed by an electric shock (500 μs, 2× threshold) applied to the supraorbital nerve as a non-conditioned stimulus (NCS). The downward arrows indicate the presence of conditioned responses (CRs). The arrowheads indicate the appearance of non-conditioned responses in eyelids. FIG. 4B shows the average percentage (±S.E.M.) of conditioned responses over 10 conditioned sessions for the four experimental groups. The results obtained for the conditioned groups are indicated with solid lines, whereas the results corresponding to the pseudo-conditioned groups are indicated with dotted lines.

The results of these experiments indicate that mangiferin and morin conserve the learning capacity after their administration to rats subjected to global ischemia, and that therefore the neuroprotective properties of both have functional consequences, conserving cognitive functions.

The invention claimed is:

1. A method for the treatment of a neurodegenerative disease in an individual in need of treatment, which comprises administering to the individual a therapeutically effective amount of a compound of formula (Ib):

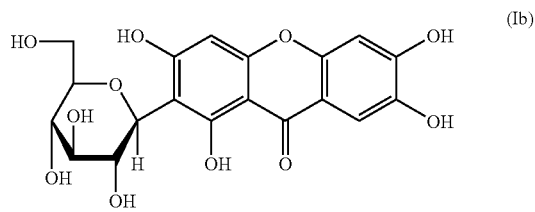

or a pharmaceutically acceptable salt thereof.

2. The method according to claim 1, wherein said neurodegenerative disease is selected from the group consisting of: cerebral ischemia, Creutzfeldt-Jakob disease, Alzheimer's disease, Huntington's disease, Lewy body disease, Parkinson's disease, Pick's disease, amyotrophic lateral sclerosis, neurofibromatosis, brain damage, cerebrovascular accident, multiple sclerosis, memory loss and multi-infarct dementia.

3. The method according to claim 2, wherein the compound of formula (Ib) is administered in combination with an additional drug useful in the treatment of a neurodegenerative disease selected from the group consisting of: cerebral ischemia, Creutzfeldt-Jakob disease, Alzheimer's disease, Huntington's disease, Lewy body disease, Parkinson's disease, Pick's disease, amyotrophic lateral sclerosis, neurofibromatosis, brain damage, cerebrovascular accident, multiple sclerosis, memory loss and multi-infarct dementia.

4. The method according to claim 3, wherein the additional drug useful in the treatment of a neurodegenerative disease selected from the group consisting of: cerebral ischemia, Creutzfeldt-Jakob disease, Alzheimer's disease, Huntington's disease, Lewy body disease, Parkinson's disease, Pick's disease, amyotrophic lateral sclerosis, neurofibromatosis, brain damage, cerebrovascular accident, multiple sclerosis, memory loss and multi-infarct dementia is administered in a form separate from the compound of formula (Ib), and wherein said administration may be simultaneous or non-simultaneous.

5. The method according to claim 1, wherein the compound of formula (Ib) is administered in combination with an additional drug useful in the treatment of a neurodegenerative disease.

6. The method according to claim 5, wherein the additional drug useful in the treatment of a neurodegenerative disease is administered in a form separate from the pharmaceutical composition comprising a compound of formula (Ib), and wherein said administration may be simultaneous or non simultaneous.

7. The method according to claim 1, wherein the compound of formula (Ib) is administered via oral, parenteral or rectal administration.

8. The method according to claim 1, wherein the compound of formula (Ib) is administered in combination with an additional drug useful in the treatment of a neurodegenerative disease.

9. The method according to claim 8, wherein the additional drug useful in the treatment of a neurodegenerative disease is administered in a form separate from the compound of formula (Ib), and wherein said administration may be simultaneous or non-simultaneous.

10. The method for the treatment of a neurodegenerative disease in an individual in need of treatment according to claim 1, which comprises administering to the individual a therapeutically effective amount of a compound of formula (Ib) so that oxidative stress in neurons is reduced.

11. A method for the treatment of neuronal oxidative stress in an individual experiencing such condition, the method comprising administering a therapeutically effective amount of a compound of formula (Ib):

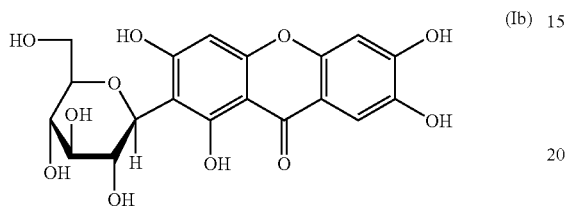

or a pharmaceutically acceptable salt thereof to the individual.

12. The method according to claim 11, wherein said neuronal oxidative stress is etiologically related to cerebral ischemia, Alzheimer's disease, or stroke in the individual.

* * * * *